United States Patent [19]
Vintzileos et al.

[11] Patent Number: 5,622,176
[45] Date of Patent: Apr. 22, 1997

[54] METHOD FOR DETERMINING THE RISK OF TRISOMY 21 IN THE SECOND TRIMESTER

[75] Inventors: Anthony M. Vintzileos, Bridgewater, N.J.; James F.X. Egan, Longmeadow, Mass.

[73] Assignee: University Of Medicine & Dentistry of NJ, Newark, N.J.

[21] Appl. No.: 507,624

[22] Filed: Jul. 26, 1995

[51] Int. Cl.$^6$ ..................................................... A61B 8/00
[52] U.S. Cl. ........................................................ 128/662.05
[58] Field of Search ............................ 128/630, 662.05, 128/660.07, 660.02; 436/510, 814

[56] References Cited

U.S. PATENT DOCUMENTS 5,506,150  4/1996  Canick et al. ........................ 436/510

*Primary Examiner*—George Manuel
*Attorney, Agent, or Firm*—Richard R. Muccino

[57] ABSTRACT

The present invention pertains to a method for the prenatal detection of trisomy 21 in the second trimester by adjusting the risk of trisomy 21 based on fetal long bone biometry which comprises the steps of (a) measuring ultrasonically the biparietal diameter and the length of the femur, humerus, tibia, and fibula bones in fetuses of a patient population in the second trimester; (b) performing amniocentesis on the patient population in step (a) to determine which fetuses are normal and which fetuses have trisomy 21; (c) from the normal fetuses, deriving equations describing the predicted lengths of the femur, humerus, tibia, and fibula based on the biparietal diameter measurements; (d) calculating a ratio of observed lengths to predicted lengths of the femur, humerus, tibia, and fibula for all fetuses; (e) comparing the ratios calculated in step (d) for normal fetuses against the ratios calculated for fetuses having trisomy 21 and determining a threshold, as a percentile of these ratios, for abnormally short bone lengths in the fetuses having trisomy 21; and (f) employing the threshold determined in step (e) to detect prenatally trisomy 21 by fetal long bone biometry. In another embodiment, the method comprises the steps of (f) employing the threshold determined in step (e) to determine sensitivity and specificity in detecting prenatally trisomy 21 by fetal long bone biometry; and (g) employing the sensitivity and specificity determined in step (f) to adjust the risk of trisomy 21.

9 Claims, 1 Drawing Sheet

The impact of ultrasound-adjusted risk for Down syndrome in the general population
(N=1,000 pregnant women-total amniocentesis rate=76/1,000)

A) 5% ≥ 35 yo (n=50)
- ↗ 20% (n=10) ≥ 40 yo, risk ≥ 1:274 even with normal U/S → AMNIO= 10
- ↘ 80% (n=40) - age 35-39
  - ↗ 80% (n=32)-normal U/S → No Amnio
  - ↘ 20% (n=8)-abn U/S → AMNIO= 8

B) 3% <35 yo, abn serum screen (n=30)
- ↗ 80% (n=24)-normal U/S
  - ↗ 50% (n=12)-risk still ≥ 1:274 → AMNIO= 12
  - ↘ 50% (n=12)-risk < 1:274 → No Amnio
- ↘ 20% (n=6)-abn U/S → AMNIO= 6

C) 70% < 35 yo, low-risk (n=700)
- ↗ 80% (n=560)-normal U/S → No amnio
- ↘ 20% (n=140)-abn U/S
  - ↗ 70% (n=100) -risk still < 1:274 → No amnio
  - ↘ 30% (n=40)-risk ≥ 1:274 → AMNIO= 40

Figure 1

The impact of ultrasound-adjusted risk for Down syndrome in the general population
(N=1,000 pregnant women-total amniocentesis rate=76/1,000)

A) 5% ≥ 35 yo
(n=50)
- ↗ 20% (n=10) ≥ 40 yo, risk ≥ 1:274 even with normal U/S → AMNIO = 10
- ↘ 80% (n=40) - age 35-39
  - ↗ 80% (n=32)-normal U/S → No Amnio
  - ↘ 20% (n=8)-abn U/S → AMNIO = 8

B) 3% <35 yo, abn serum screen
(n=30)
- ↗ 80% (n=24)-normal U/S
  - ↗ 50% (n=12)-risk still ≥ 1:274 → AMNIO = 12
  - ↘ 50% (n=12)-risk < 1:274 → No Amnio
- ↘ 20% (n=6)-abn U/S → AMNIO = 6

C) 70% < 35 yo, low-risk
(n=700)
- ↗ 80% (n=560)-normal U/S → No amnio
- ↘ 20% (n=140)-abn U/S
  - ↗ 70% (n=100) -risk still < 1:274 → No amnio
  - ↘ 30% (n=40)-risk ≥ 1:274 → AMNIO = 40

METHOD FOR DETERMINING THE RISK OF TRISOMY 21 IN THE SECOND TRIMESTER

BACKGROUND OF THE INVENTION

1. Field of the Invention

This invention relates to a method for the prenatal detection of trisomy 21 in the second trimester by adjusting the risk of trisomy 21 based on fetal long bone biometry. More particularly, this invention relates to (a) measuring ultrasonically the biparietal diameter and the length of the femur, humerus, tibia, and fibula bones in fetuses of a patient population in the second trimester; (b) performing amniocentesis on the patient population in step (a) to determine which fetuses are normal and which fetuses have trisomy 21; (c) from the normal fetuses, deriving equations describing the predicted lengths of the femur, humerus, tibia, and fibula based on the biparietal diameter measurements; (d) calculating a ratio of observed lengths to predicted lengths of The femur, humerus, tibia, and fibula for all fetuses; (e) comparing the ratios calculated in step (d) for normal fetuses against the ratios calculated for fetuses having trisomy 21 and determining a threshold, as a percentile of these ratios, for abnormally short bone lengths in the fetuses having trisomy 21; and (f) employing the threshold determined in step (e) to detect prenatally trisomy 21 by fetal long bone biometry. In another embodiment, the method comprises the steps of (f) employing the threshold determined in step (e) to determine sensitivity and specificity in detecting prenatally trisomy 21 by fetal long bone biometry; and (g) employing the sensitivity and specificity determined in step (f) to adjust the risk of trisomy 21.

2. Description of the Background

The disclosures referred to herein to illustrate the background of the invention and to provide additional detail with respect to its practice are incorporated herein by reference. For convenience, the disclosures are referenced in the following text and respectively grouped in the appended bibliography.

Trisomy 21 (trisomy G, Down's syndrome, mongolism) is a condition characterized by a small, anteroposteriorly flattened skull, short, flat-bridged nose, epicanthal fold, short phalanges, and widened space between the first and second digits of hands and feet, with moderate to severe retardation, and associated with a chromosomal abnormality. In about 85% of cases of trisomy 21, there is an extra chromosome 21. Typically, the affected children are born to older mothers, but sporadic or trisomic mongolism may also occur in children of young mothers. The overall incidence of trisomy 21 is about 1:700 live births, but there is a marked variability depending on maternal age. In the early child-bearing years, the incidence of trisomy 21 is about 1:2000 live births whereas for mothers over 40, the incidence rises to about 45:1000 live births. Close to 50% of infants with trisomy 21 are born to mothers over 35. Nevertheless, recent studies have shown that the extra chromosome 21 can occasionally come from the father.

The use of ultrasonography in the prenatal detection of fetuses with trisomy 21 has been the subject of several reports [1-17]. The combination of various ultrasound markers for trisomy 21 has increased the sensitivity to 83%–91% with relatively low false positive rates ranging between 10% and 20% [2,16]. As a result, the use of ultrasound to adjust the risk for trisomy 21 has been advocated, and therefore the need for genetic amniocentesis in low as well as high risk patients [16-17]. In general, this approach requires special expertise which has prevented the incorporation of the "genetic" ultrasound into general practice. Although specific expertise is not required for measuring the femur, humerus, renal pelvis, or nuchal fold thickening, it is clear that expertise and experience are required to assess hypoplasia of the middle phalanx of the fifth digit, wide space between the first and second toe, and to diagnose structural malformations, especially cardiac defects. Therefore, simplification of sonographic detection of trisomy 21 would be desirable and would enhance the clinical applicability. Although there are several accounts reporting that fetuses with trisomy 21 are more likely to have short femur or humerus, there are no reports regarding the usefulness of tibia and/or fibula measurements in the prenatal detection of trisomy 21.

BRIEF DESCRIPTION OF THE FIGURE AND TABLES

FIG. 1 illustrates the impact of ultrasound adjusted risk for trisomy 21 in the general population.

Table I illustrates regression equations for the expected long bone measurement (dependent variable) based on the measured BPD (independent variable).

Table II illustrates abnormal cut-off values of long bone measurements for a given BPD.

Table III illustrates efficacy of long bone measurements alone and in combination in detecting fetal trisomy 21.

Table IV illustrates long bone findings in trisomy 21 fetuses.

Table V illustrates efficacy of fetal long bone biometry to detect fetal trisomy 21 according to maternal age.

Table VI illustrates midtrimester risk for trisomy 21 based on maternal age in a structurally normal fetus as modified by ultrasonic measurements of fetal long bones.

Table VII illustrates midtrimester risk for trisomy 21 based on triple screen in a structurally normal fetus as modified by ultrasonic measurements of fetal long bones.

SUMMARY OF THE INVENTION

The present invention pertains to a method for the prenatal detection of trisomy 21 in the second trimester by adjusting the risk of trisomy 21 based on fetal long bone biometry which comprises the steps of:

(a) measuring ultrasonically the biparietal diameter and the length of the femur, humerus, tibia, and fibula bones in fetuses of a patient population in the second trimester;

(b) performing amniocentesis on the patient population in step (a) to determine which fetuses are normal and which fetuses have trisomy 21;

(c) from the normal fetuses, deriving equations describing the predicted lengths of the femur, humerus, tibia, and fibula based on the biparietal diameter measurements;

(d) calculating a ratio of observed lengths to predicted lengths of the femur, humerus, tibia, and fibula for all fetuses;

(e) comparing the ratios calculated in step (d) for normal fetuses against the ratios calculated for fetuses having trisomy 21 and determining a threshold, as a percentile of these ratios, for abnormally short bone lengths in the fetuses having trisomy 21; and (f) employing the threshold determined in step (e) to detect prenatally trisomy 21 by fetal long bone biometry.

The present invention also pertains to a method for the prenatal detection of trisomy 21 in the second trimester by adjusting the risk of trisomy 21 based on fetal long bone biometry which comprises the steps of:

(a) measuring ultrasonically the biparietal diameter and the length of the femur, humerus, tibia, and fibula bones in fetuses of a patient population in the second trimester;

(b) performing amniocentesis on the patient population in step (a) to determine which fetuses are normal and which fetuses have trisomy 21;

(c) from the normal fetuses, deriving equations describing the predicted lengths of the femur, humerus, tibia, and fibula based on the biparietal diameter measurements;

(d) calculating a ratio of observed lengths to predicted lengths of the femur, humerus, tibia, and fibula for all fetuses;

(e) comparing the ratios calculated in step (d) for normal fetuses against the ratios calculated for fetuses having trisomy 21 and determining a threshold, as a percentile of these ratios, for abnormally short bone lengths in the fetuses having trisomy 21;

(f) employing the threshold determined in step (e) to determine sensitivity and specificity in detecting prenatally trisomy 21 by fetal long bone biometry; and (g) employing the sensitivity and specificity determined in step (f) to adjust the risk of trisomy 21.

DETAILED DESCRIPTION OF THE INVENTION

In accord with the present invention, applicants have established the efficacy of long bone biometry, including measurements of femur, humerus, tibia and fibula, in detecting trisomy 21 in the second trimester of pregnancy by adjusting the risk of trisomy 21 and have generated tables that allow adjusting the risk for trisomy 21, and therefore the need for genetic amniocentesis, depending on fetal long bone biometry. Four long bones, femur, humerus, tibia and fibula, were ultrasonically measured in singleton fetuses prior to genetic amniocentesis. Fetuses with normal karyotypes were used to derive regression equations describing predicted femur, humerus, tibia and fibula on the basis of the biparietal diameter (BPD) measurement. Observed to expected long bone ratios were calculated for each fetus and short bones were defined as less than the tenth percentiles of these ratios. The efficacy of each abnormally short bone alone, and in combination, was determined in 22 fetuses with trisomy 21 encountered during the study period. After the sensitivity and specificity of long bone biometry was established, appropriate tables were generated by Bayes' theorem to adjust the risk for trisomy 21 in the second trimester depending on long bone biometry. Outcome information included the results of fetal karyotypes obtained by genetic amniocentesis.

A total of 515 patients between 14 and 23 weeks gestation were included in the study. Of these, 493 had normal fetal karyotype and 22 had trisomy 21. The thresholds in terms of observed to expected ratios used to define an abnormally short bone were: femur length <0.88, humerus length <0.89, tibia length <0.86, and fibula length <0.86. Using these thresholds, the sensitivity, specificity, positive and negative predictive values of the femur were 22.7%, 89.9%, 9%, 96.3%; humerus 45.5%, 90%, 17%, 97.4%, tibia 27.3%, 91.3%, 12.2%, 96.6%; and fibula 18.2%, 91%, 8.3%, 96.2%, respectively. The sensitivity of an abnormal ultrasound, as defined by the presence of one or more short bones, was 63.6%, the specificity 78.5%, the positive predictive value 11.7%, and the negative predictive value 98%. The sensitivity and specificity of long bone biometry was independent of maternal age. According to Bayes' theorem, genetic amniocentesis may not be recommended for women under 40 years old in the presence of normal long bone biometry (all four bones normal). In summary, second trimester fetal long bone biometry is useful in detecting trisomy 21 and may be used to adjust the a priori risk of both high and low risk women for trisomy 21 and therefore the need for genetic amniocentesis.

Results

The study consisted of 515 fetuses, 493 were karyotypically normal and 22 had trisomy 21. The maternal age was 34.8±4.9 (mean±SD) years and the gestational age at the time of amniocentesis was 17.3±1.6 (mean+SD) weeks. Indications for genetic amniocentesis included advanced maternal age (65%), abnormal serum screening (26%), and other indications (9%). The regression equations for determining the expected (predicted) value of each bone measurement according to the measured BPD are shown in Table I. The abnormal observed to expected ratios (thresholds) were as follows: short femur<0.88, short humerus<0.89, short tibia<0.86, and short fibula<0.86. Table II shows the specific thresholds for a wide range of BPD measurements. Using these thresholds, the sensitivity, specificity, positive and negative predictive values of each bone alone, and in combination, in detecting trisomy 21 were calculated (Table III). Table IV describes in detail the long bone findings in trisomy 21 fetuses. Since application of the Bayes' theorem requires conditional independence (i.e., maternal age independence) the next step was to determine if the sensitivity and specificity varied according to maternal age. Table V shows that there were no differences in the sensitivity or specificity of long bone biometry between women under 36 versus women 36 years old or older. Using the sensitivities and specificities established in Table III, Bayes' theorem was applied to generate risk estimates for trisomy 21 on the basis of fetal long bone biometry combined with either maternal age (Table VI) or serum biochemical screening (Table VII). As shown, of the individual bones, a short humerus had the highest sensitivity (45.5%), whereas the sensitivity of using "one or more abnormally short bones" as the abnormal test was 63.6%, with a specificity of 78.5%

Discussion

Prenatal diagnosis of trisomy 21 in the second trimester of pregnancy has traditionally relied on amniocentesis in women 35 years of age or older. Using maternal age as a screening method, however, will identify only 20% of trisomy 21 cases with a false positive rate of approximately 5–7%. It is generally accepted that the average pregnancy loss associated with genetic amniocentesis is approximately 1 in 270. When advanced maternal age alone is used to screen for trisomy 21, approximately 140 amniocenteses are required to discover one fetus with trisomy 21[17]. This implies that one normal fetus may be lost for every two fetuses identified with trisomy 21. In recent years, the combination of maternal age and serum biochemical screening (maternal serum alpha-fetoprotein, estriol, human chorionic gonadotropin) has been shown to identify approximately 60–65% of fetuses with trisomy 21[20]. This approach has false positive rates ranging from 5–10% but still does not focus on the right group of candidates for amniocentesis because approximately 60–70 amniocenteses are needed to detect one fetus with trisomy 21[17]. Thus, even with the most current screening techniques, one normal fetus may be lost as a complication of genetic amniocentesis for every three to four fetuses identified with trisomy 21. It is therefore desirable to develop techniques to optimize selection of candidates for invasive prenatal testing in order to decrease procedure-related losses of normal fetuses without significantly reducing detection rates.

In one study, the English literature was reviewed and established the overall sensitivity and specificity of sonographic markers of fetal aneuploidy in order to generate tables for adjusting the risk for trisomy 21[17]. According to that review, high sensitivities (83–91%) for detecting trisomy 21 were reported by experienced investigators[17]. Therefore, the prerequisite for such an ultrasound examination is skill and experience in diagnosing fetal structural malformations and especially congenital heart disease. Such an expertise, however, is not widely available. As a result, ultrasound adjustment of the risk for trisomy 21 has not been incorporated into general practice. The purpose of this study was to report a simple method for adjusting trisomy 21 risk using four fetal bones i.e., femur, humerus, tibia, and fibula. The advantage of this approach is that great expertise usually is not required for identifying and measuring a long bone. However, the accuracy of these measurements and the applicability of the ratios may vary between different ultrasound units or different populations. Therefore, each institution should establish their patient thresholds for defining "shortness" of a particular bone.

The present study established thresholds for defining "shortness" for femur, humerus, tibia, and fibula in our own patient population. Using these thresholds, when one or more of these bones are abnormally short, the risk for trisomy 21 is increased. On the other hand, a normal long bone biometry (all four bones normal) theoretically decreases the a priori risk for trisomy 21 by approximately 63%. Adjusting the risk for trisomy 21 based upon fetal long bone biometry is a simple method which may lead to increased or decreased risk for individual patients. For instance, many low risk women who have an ultrasound for other indications may be found to have short one or more fetal bones and therefore at increased risk for trisomy 21. On the other hand, if the currently accepted risk (1:274) of a 35 year old woman is used as an indication for offering genetic amniocentesis, genetic amniocentesis may not be considered in the presence of normal long bone biometry except in women 40 years old or older. This ultrasound risk adjustment may lead to better selection of candidates for amniocentesis with higher yields of positive amniocentesis results, thus minimizing the procedure-related losses of normal fetuses. As shown in Table IV, a short fibula did not add to the overall detection rate. However, a larger number of fetuses with trisomy 21 need to be accumluated before a final decision can be made that fibula measurements should be omitted. Consequently, fibula was kept as one of the four bones to be measured to adjust risks.

The adjusted risks in Tables VI and VII assume the absence of gross fetal structural malformations, although in our 22 trisomy 21 cases two were found to have small ventricular septal defects and one had abnormal nuchal fold thickening during the basic scanning performed prior to amniocentesis. It should be emphasized that the risks illustrated in Tables VI and VII are based in mathematic modeling and, therefore, are purely theoretical and may change appreciably once large prospective studies become available. Patients should be counseled that with this approach, some cases with trisomy 21 may be missed.

The routine use of these tables on every patient who has second trimester ultrasonography should neither increase nor decrease the total number of amnioceteses. The impact of ultrasound adjusted risk for trisomy 21 in the general population is illustrated in FIG. 1. In deriving the algorithm of FIG. 1, the following assumptions were made: I) Approximately 5% of the pregnant population are women 35 years old or older; of these, approximately 80% are between the ages 35–39; and approximately 20% are 40 years old or older. Women who are 40 years old or older regardless of the ultrasound results, even with normal long bone biometry, have a risk for trisomy 21 greater than or equal to 1:274 and therefore should be offered amniocentesis. However, approximately 80% of the advanced maternal age population are women between the ages 35–39. Of these women, 80% would have a normal ultrasound with an adjusted risk of less than 1:274 and, therefore, would not be candidates for amniocentesis. The remaining 20% would have abnormal ultrasound and therefore, should be offered amniocentesis period. 2) Approximately 3% of the population are women under 35 years old who are at increased risk for trisomy 21 based upon abnormal serum screening. Of these women, 20% would have abnormal ultrasound and should be lo offered amniocentesis, whereas the remaining 80% would have a normal ultrasound. In approximately half of the patients with normal ultrasound, the risk may still be greater than or equal to 1:274 and therefore amniocentesis may be offered; whereas in the remaining 50% the risk may become less than 1:274 and amniocentesis may not be needed; 3) The third group of women that an ultrasound-adjusted risk for trisomy 21 may be indicated for is the low risk population of women younger than 35 years of age. Approximately 70% of these women may have a second trimester sonogram for some other indication. Approximately 80% will have a normal ultrasound and therefore amniocentesis is not medically indicated. The remaining 20% will have an abnormal ultrasound. In approximately 70% of these cases, the risk may still be less than 1:274 and amniocentesis may not be indicated, whereas in the remaining 30% the risk may become greater than or equal to 1:274 and an amniocentesis may be offered. If the above assumptions are correct, the total amniocentesis rate generated by routinely incorporating the ultrasound-adjusted risk for trisomy 21 on every patient who has ultrasonography is 76/1,000 or 7.6%. This rate is not different from the rate of 80/1,000 (or 8%) generated by the current practice of offering routinely amniocentesis to women 35 years old or older and to all younger women with abnormal serum screening. The end result, however, may be better selection of candidates for an invasive procedure with known complications.

The most compelling argument for the use of individualized ultrasound-adjusted risks is respect for maternal autonomy. Since the risk of having a child with trisomy 21 may not have the same significance compared to the risk of losing a normal fetus (as a result of genetic amniocentesis) for all patients, individualization of the degree of risks should be part of the informed consent. It is the physician's duty to provide all necessary information to the patient and proceed with an invasive genetic procedure only if the couple agrees. It should not be the physician's position to recommend for or against amniocentesis. This is an individual decision which should be made by the patient and not the physician. Ultrasonography by simple fetal bone biometry may help in individualizing the informed consent process of these patients.

The present invention is further illustrated by the following examples which are not intended to limit the effective scope of the claims. All parts and percentages in the examples and throughout the specification and claims are by weight of the final composition unless otherwise specified.

EXAMPLES

Materials and Methods

This study was conducted in the Antenatal Testing Units of the University of Connecticut Health Center, Farmington, Conn. and Robert Wood Johnson Medical School/St Peter's Medical Center, New Brunswick, N.J. All patients were referred to both units for second trimester genetic amniocentesis between 14 and 23 weeks gestation. In all cases, the estimated gestational age as established by the last menstrual period was within two weeks of the sonographic gestational age. Fetuses with gross ultrasound anomalies, as well as fetuses with chromosome abnormalities other than trisomy 21, were excluded. Only singleton pregnancies were included in this study. The ultrasound equipment used were Acuson 128 (Acuson Computed Sonography, Mountain View, Calif.), Ultramark-9 (Advanced Technology Laboratories, Bothell, Wash.), or Aloka 650 (Corometrics Medical Systems, Wallingford, Conn.) with freeze-frame capabilities and on-screen calipers. A 3.5 or 5-MHZ linear or curvilinear transducer was used for scanning. Measurements obtained at each examination included biparietal diameter (BPD), head circumference, abdominal circumference, femur length (FL), humerus length (HL), tibia length (TL) and fibula length (FiL). The BPD was measured in a transverse plane, from the outer edge to the inner edge of the skull at the level of the thalami. The long bones were measured in a standard method that includes the diaphyseal portion of the shaft. The differentiation between tibia and fibula was based on the fact that the tibia is longer and originates more proximally than the fibula at the knee. Outcome information included the results of fetal karyotypes as determined by genetic amniocentesis. The group of normal fetuses was used to derive linear regression equations relating the expected (predicted) bone measurement according to BPD for all four bones. The observed to expected ratio was determined for each fetus and the tenth percentile was used as the threshold for defining an abnormally short bone. Using these thresholds, the sensitivity, specificity, positive and negative predictive values of each bone alone, and in combination, were then calculated to detect trisomy 21. The next step was to confirm that the sensitivities and specificities were maternal age independent. Bayes' theorem was then applied to derive the adjusted risk for trisomy 21 on the basis of the a priori risk related to maternal age or abnormal triple screen values. According to Bayes' theorem, the probability of disease (trisomy 21), given a positive test, is the product of the probability of a positive test in a given disease (sensitivity) times the probability of disease (prevalence or a priori risk) divided by the probability of the positive test [18,19]. This theorem may be expressed by the following formula:

Adjusted risk for trisomy 21=sensitivity×a priori risk divided by [(sensitivity)×a priori risk]+([1−specificity])×[1−a priori risk)].

On the basis of this formula, Tables were generated to adjust the risk estimate for trisomy 21 on the basis of abnormal fetal long bone biometry defined as the presence of one or more abnormally short bones. The risk was also adjusted in the presence of normal ultrasonography (all four bones normal) by using the formula (1-negative predictive value). The negative predictive value was calculated as follows:[18,19]

Negative predictive value=specificity×(1−a priori risk) divided by (specificity×|1−a priori risk|)+([1 sensitivity]×[a priori risk])

Statistical analyses were performed using Excel (Microsoft Corporation, Redmond, Wash.) and StatView SE+graphics TM (Abacus Concepts, Inc., Berkeley, Calif.) on a Macintosh PC (Apple computers, Cupertino, Calif.). In addition to Bayes' theorem, the statistical analyses included descriptive statistics, test of proportions and 2×2 contingency tables to calculate the sensitivity, specificity, positive and negative predictive values of each bone alone, and in combination. A p value <0.05 was considered significant.

TABLE I

Regression equations for the expected long bone measurement (dependent variable) based on the measured BPD (independent variable)

| | | R | $R^2$ | P |
|---|---|---|---|---|
| Expected FL = | 0.87 (BPD) − 1.01 | 0.91 | 0.83 | 0.0001 |
| Expected HL = | 0.79 (BPD) − 0.69 | 0.91 | 0.82 | 0.0001 |
| Expected TL = | 0.79 (BPD) − 1.04 | 0.90 | 0.81 | 0.0001 |
| Expected Fil = | 0.80 (BPD) − 1.19 | 0.90 | 0.82 | 0.0001 |

FL = femur length; HL = humerus length; TL = tibia length; Fil = fibula length; BPD = biparietal diameter

TABLE II

Abnormal cut-off values of long bone measurements for a given BPD

| BPD (cm) | Femur length (cm) | Humerus length (cm) | Tibia length (cm) | Fibula length (CM) |
|---|---|---|---|---|
| 2.0 | 0.64 | 0.79 | 0.46 | 0.35 |
| 2.1 | 0.72 | 0.86 | 0.53 | 0.42 |
| 2.2 | 0.80 | 0.93 | 0.60 | 0.49 |
| 2.3 | 0.87 | 1.00 | 0.67 | 0.56 |
| 2.4 | 0.95 | 1.07 | 0.74 | 0.63 |
| 2.5 | 1.03 | 1.14 | 0.80 | 0.70 |
| 2.6 | 1.10 | 1.21 | 0.87 | 0.77 |
| 2.7 | 1.18 | 1.28 | 0.94 | 0.83 |
| 2.8 | 1.25 | 1.35 | 1.01 | 0.90 |
| 2.9 | 1.33 | 1.42 | 1.08 | 0.97 |
| 3.0 | 1.41 | 1.50 | 1.14 | 1.04 |
| 3.1 | 1.48 | 1.57 | 1.21 | 1.11 |
| 3.2 | 1.56 | 1.64 | 1.28 | 1.18 |
| 3.3 | 1.64 | 1.71 | 1.35 | 1.25 |
| 3.4 | 1.71 | 1.78 | 1.42 | 1.32 |
| 3.5 | 1.79 | 1.85 | 1.48 | 1.38 |
| 3.6 | 1.87 | 1.92 | 1.55 | 1.45 |
| 3.7 | 1.94 | 1.99 | 1.62 | 1.52 |
| 3.7 | 1.94 | 1.99 | 1.62 | 1.52 |
| 3.8 | 2.02 | 2.06 | 1.69 | 1.59 |
| 3.9 | 2.10 | 2.13 | 1.76 | 1.66 |
| 4.0 | 2.17 | 2.20 | 1.82 | 1.73 |
| 4.1 | 2.25 | 2.27 | 1.89 | 1.80 |
| 4.2 | 2.33 | 2.34 | 1.96 | 1.87 |
| 4.3 | 2.40 | 2.41 | 2.03 | 1.94 |
| 4.4 | 2.48 | 2.48 | 2.09 | 2.00 |
| 4.5 | 2.56 | 2.55 | 2.16 | 2.07 |
| 4.6 | 2.63 | 2.62 | 2.23 | 2.14 |
| 4.7 | 2.71 | 2.69 | 2.30 | 2.21 |

TABLE II-continued

Abnormal cut-off values of long bone measurements for a given BPD

| BPD (cm) | Femur length (cm) | Humerus length (cm) | Tibia length (cm) | Fibula length (CM) |
|---|---|---|---|---|
| 4.8 | 2.79 | 2.76 | 2.37 | 2.28 |
| 4.9 | 2.86 | 2.83 | 2.43 | 2.35 |
| 5.0 | 2.94 | 2.90 | 2.50 | 2.42 |
| 5.1 | 3.02 | 2.97 | 2.57 | 2.49 |
| 5.2 | 3.09 | 3.04 | 2.64 | 2.55 |
| 5.3 | 3.17 | 3.11 | 2.71 | 2.62 |
| 5.4 | 3.25 | 3.18 | 2.77 | 2.69 |
| 5.5 | 3.32 | 3.25 | 2.84 | 2.76 |
| 5.6 | 3.40 | 3.32 | 2.91 | 2.83 |
| 5.7 | 3.48 | 3.39 | 2.98 | 2.90 |
| 5.8 | 3.55 | 3.46 | 3.05 | 2.97 |
| 5.9 | 3.63 | 3.53 | 3.11 | 3.04 |
| 6.0 | 3.70 | 3.60 | 3.18 | 3.10 |

TABLE III

Efficacy of long bone measurements alone and in combination in detecting fetal trisomy 21

| Definition of abnormal test | Sensitivity | Specificity | Positive Predictive Value | Negative Predictive Value |
|---|---|---|---|---|
| Short Femur (O/E < 0.88) | 5/22 (22.7%) | 443/493 (89.9%) | 5/55 (9%) | 443/460 (96.3%) |
| Short Humerus (O/E < 0.89) | 10/22 (45.5%) | 444/493 (90%) | 10/59 (17%) | 444/456 (97.4%) |
| Short Tibia (O/E < 0.86) | 6/22 (27.3%) | 450/493 (91.3%) | 6/49 (12.2%) | 450/466 (96.6%) |
| Short Fibula (O/E < 0.86) | 4/22 (18.2%) | 449/493 (91%) | 4/48 (8.3%) | 449/467 (96.2%) |
| ≧1 short bones | 14/22 (63.6%) | 387/493 (78.5%) | 14/120 (11.7%) | 387/395 (98%) |
| ≧2 short bones | 8/22 (36.4%) | 447/493 (90.7%) | 8/54 (14.8%) | 447/461 (97%) |

O/E = Observed-to-expected ratio according to a given BPD measurement (See Table II).

TABLE IV

Long bone findings in trisomy 21 fetuses

| INDICATION | GESTATIONAL AGE (weeks) | FEMUR | HUMERUS | TIBIA | FIBULA |
|---|---|---|---|---|---|
| Serology | 18.1 | normal | normal | normal | normal |
| AMA | 19.0 | normal | normal | normal | normal |
| AMA & serology | 18.0 | normal | normal | normal | normal |
| Serology | 22.0 | normal | normal | normal | normal |
| AMA | 15.9 | normal | normal | normal | normal |
| Serology | 18.6 | normal | normal | normal | normal |
| Serology | 19.3 | normal | normal | normal | normal |
| AMA | 18.3 | normal | normal | normal | normal |
| AMA | 16.4 | short | normal | normal | normal |
| AMA | 16.7 | short | short | normal | normal |
| AMA | 16.4 | short | short | normal | normal |
| AMA | 15.6 | short | short | normal | short |
| AMA | 17.0 | normal | short | normal | normal |
| AMA | 16.4 | normal | normal | short | normal |
| AMA | 16.7 | normal | short | short | normal |
| Serology | 16.9 | normal | short | short | normal |
| Serology | 15.9 | normal | short | normal | normal |
| Serology | 18.7 | normal | short | normal | normal |
| AMA & serology | 17.0 | normal | short | normal | normal |
| AMA & serology | 18.4 | normal | normal | short | short |
| AMA & serology | 17.6 | normal | normal | short | short |
| AMA | 14.9 | short | short | short | short |

AMA = Advanced maternal age

TABLE V

Efficacy of fetal long bone biometry to detect trisomy 21 according to maternal age

|  | MATERNAL AGE (years) <36 (N = 238) | MATERNAL AGE (years) ≧36 (N = 277) | P |
|---|---|---|---|
| SHORT FEMUR |  |  |  |
| Sensitivity | 2/12 (16.7%) | 3/10 (30%) | NS |
| Specificity | 205/226 (90.7%) | 238/267 (89.1%) | NS |
| SHORT HUMERUS |  |  |  |
| Sensitivity | 6/11 (54.5%) | 4/11 (36.4%) | NS |
| Specificity | 209/226 (92.5%) | 235/267 (88%) | NS |
| SHORT TIBIA |  |  |  |
| Sensitivity | 3/11 (27.3%) | 3/11 (27.3%) | NS |
| Specificity | 206/226 (91.1%) | 244/267 (91.4%) | NS |

TABLE V-continued

Efficacy of fetal long bone biometry to detect trisomy 21 according to maternal age

|  | MATERNAL AGE (years) <36 (N = 238) | MATERNAL AGE (years) ≧36 (N = 277) | P |
|---|---|---|---|
| SHORT FIBULA |  |  |  |
| Sensitivity | 2/11 (18.2%) | 2/11 (18.2%) | NS |
| Specificity | 209/226 (92.5%) | 240/267 (89.9%) | NS |
| ≧1 SHORT BONES |  |  |  |
| Sensitivity | 7/11 (63.6%) | 7/11 (63.6%) | NS |
| Specificity | 181/226 (80%) | 206/267 (77.1%) | NS |
| ≧2 SHORT BONES |  |  |  |
| Sensitivity | 4/11 (36.4%) | 4/11 (36.4%) | NS |
| Specificity | 209/226 (92.5%) | 238/267 (89.1%) | NS |

NS = Not Significant

TABLE VI

Midtrimester risk for trisomy 21 based on maternal age in a structurally normal fetus as modified by ultrasonic measurements of fetal long bones.
(All risks are expressed as 1/x)

| Maternal Age | Age alone* | All four bones normal | Short Femur | Short Humerus | Short Tibia | Short Fibula | ≧2 Short Bones** |
|---|---|---|---|---|---|---|---|
| 20 | 1,231 | 3,742 | 769 | 375 | 554 | 851 | 439 |
| 21 | 1,145 | 3,481 | 715 | 349 | 515 | 791 | 409 |
| 22 | 1,065 | 3,238 | 665 | 324 | 479 | 736 | 380 |
| 23 | 1,000 | 3,040 | 625 | 305 | 450 | 691 | 357 |
| 24 | 942 | 2,863 | 588 | 287 | 424 | 651 | 336 |
| 25 | 887 | 2,696 | 554 | 270 | 399 | 613 | 317 |
| 26 | 842 | 2,559 | 526 | 257 | 379 | 582 | 301 |
| 27 | 798 | 2,426 | 499 | 243 | 359 | 552 | 285 |
| 28 | 755 | 2,295 | 472 | 230 | 340 | 522 | 270 |
| 29 | 721 | 2,191 | 451 | 220 | 325 | 498 | 258 |
| 30 | 685 | 2,082 | 428 | 209 | 308 | 474 | 245 |
| 31 | 650 | 1,975 | 406 | 198 | 293 | 449 | 232 |
| 32 | 563 | 1,711 | 352 | 172 | 254 | 389 | 201 |
| 33 | 452 | 1,373 | 283 | 138 | 204 | 313 | 162 |
| 34 | 352 | 1,069 | 220 | 108 | 159 | 244 | 126 |
| 35 | 274 | 832 | 172 | 84 | 124 | 190 | 98 |
| 36 | 213 | 647 | 133 | 65 | 96 | 148 | 77 |
| 37 | 166 | 504 | 104 | 51 | 75 | 115 | 60 |
| 38 | 129 | 391 | 81 | 40 | 59 | 90 | 47 |
| 39 | 100 | 303 | 63 | 31 | 46 | 70 | 36 |
| 40 | 78 | 236 | 49 | 24 | 36 | 54 | 29 |
| 41 | 61 | 184 | 39 | 19 | 28 | 43 | 22 |
| 42 | 47 | 142 | 30 | 15 | 22 | 33 | 17 |
| 43 | 37 | 111 | 24 | 12 | 17 | 26 | 14 |
| 44 | 29 | 87 | 19 | 10 | 14 | 21 | 11 |
| 45 | 22 | 66 | 14 | 7 | 11 | 16 | 9 |
| 46 | 17 | 51 | 11 | 6 | 8 | 12 | 7 |
| 47 | 13 | 38 | 9 | 5 | 7 | 9 | 5 |
| 48 | 10 | 29 | 7 | 4 | 5 | 7 | 4 |
| 49 | 8 | 23 | 6 | 3 | 4 | 6 | 4 |

*adapted from Palomaki GE, Haddow JE: Am J Obstet Gynecol 1987; 156:460–463.
**If the humerus is one of the short bones, use the "Short Humerus" column.

TABLE VII

Midtrimester risk for trisomy 21 based on triple screen in a structurally normal fetus as modified by ultrasonic measurements of fetal long bones.
(All risks are expressed as 1/x)

| Triple screen risk | All four bones normal | Short Femur | Short Humerus | Short Tibia | Short Fibula | ≧2 Short Bones* |
|---|---|---|---|---|---|---|
| 15,000 | 44,928 | 9362 | 4277 | 6741 | 10360 | 5347 |
| 14,500 | 43,430 | 9050 | 4135 | 6516 | 10014 | 5168 |
| 14,000 | 41,933 | 8738 | 3992 | 6292 | 9669 | 4990 |
| 13,500 | 40,435 | 8426 | 3850 | 6067 | 9324 | 4812 |
| 13,000 | 38,937 | 8114 | 3707 | 5842 | 9878 | 4634 |
| 12,500 | 37,440 | 7802 | 3565 | 5618 | 8633 | 4456 |
| 12,000 | 35,942 | 7490 | 3422 | 5393 | 8288 | 4277 |
| 11,500 | 34,444 | 7177 | 3280 | 5168 | 7942 | 4099 |
| 11,000 | 32,947 | 6865 | 3137 | 4943 | 7597 | 3921 |
| 10,500 | 31,449 | 6553 | 2994 | 4719 | 7252 | 3743 |
| 10,000 | 29,952 | 6241 | 2852 | 4494 | 6907 | 3565 |
| 9,500 | 28,454 | 5929 | 2709 | 4269 | 6561 | 3386 |
| 9,000 | 26,956 | 5617 | 2567 | 4045 | 6216 | 3208 |
| 8,500 | 25,459 | 5305 | 2424 | 3820 | 5871 | 3030 |
| 8,000 | 23,961 | 4993 | 2282 | 3595 | 5525 | 2852 |
| 7,500 | 22,463 | 4681 | 2139 | 3371 | 5180 | 2674 |
| 7,000 | 20,966 | 4369 | 1997 | 3146 | 4835 | 2495 |
| 6,500 | 19,468 | 4057 | 1854 | 2921 | 4489 | 2317 |
| 6,000 | 17,970 | 3745 | 1711 | 2697 | 4144 | 2139 |
| 5,500 | 16,473 | 3433 | 1569 | 2472 | 3799 | 1961 |
| 5,000 | 14,975 | 3121 | 1426 | 2247 | 3454 | 1783 |
| 4,500 | 16,478 | 2809 | 1284 | 2023 | 3108 | 1604 |
| 4,000 | 11,980 | 2497 | 1141 | 1798 | 2763 | 1426 |
| 3,500 | 10,482 | 2185 | 999 | 1573 | 2418 | 1248 |
| 3,000 | 8,985 | 1873 | 856 | 1649 | 2072 | 1070 |
| 2,500 | 7,487 | 1561 | 714 | 1124 | 1727 | 892 |
| 2,000 | 5,989 | 1249 | 571 | 899 | 1382 | 714 |
| 1,500 | 4,492 | 937 | 428 | 675 | 1036 | 535 |
| 1,000 | 2,994 | 625 | 286 | 450 | 691 | 357 |
| 500 | 1,496 | 313 | 143 | 225 | 346 | 179 |

*If the humerus is one of the short bones, use the "Short Humerus" column.

Appendium of References

1. Nyberg D A, Resta R G, Luthy D A, Hickok D E, Mahony B S, Hirsch J H. Prenatal sonographic findings of Down syndrome: Review of 94 cases. Obstet Gynecol 1990;76:370–7.

2. Benacerraf B R, Neuberg D, Bromley B, Frigoletto F D. Sonographic scoring index for prenatal detection of chromosomal abnormalities. J Ultrasound Med 1992; 11:449–58.

3. Lockwood C, Benacerraf B, Krinsky A, et at. A sonographic screening method for Down syndrome. Am J Obstet Gynecol 1987; 157:803–8.

4. Perrella R, Duerinck A J, Grant E G, Tessler F, Tabsh K, Crandall BF. Second-trimester sonographic diagnosis of Down syndrome: Role of femur-length shortening and nuchal-fold thickening. AJR 1988; 151:981–5.

5. Dicke J M, Gray D L, Songster G S, Crane S P. Fetal biometry as a screening tool for the detection of chromosomally abnormal pregnancies. Obstet Gynecol 1989;74:726–9.

6. Rodis J F, Vintzileos A M, Fleming A D, et at. Comparison of humerus length versus femur length in fetuses with Down syndrome. Am J Obstet Gynecol 1991;164:1051–6.

7. Rotmensch S, Luo J S, Liberati M, Belanger K, Mahoney M J, Hobbins JC. Fetal humeral length to detect Down syndrome. Am J Obstet Gynecol 1992; 166: 13304.

8. Nyberg D A, Resta R G, Luthy D A, Hickok D E, Williams M A. Humerus and femur length shortening in the detection of Down's syndrome. Am J Obstet Gynecol 1993;168:534–8.

9. Benacerraf B R, Mandell J, Estroff J A, Harlow B L, Frigoletto FD. Fetal pyelectasis: A possible association with Down syndrome. Obstet Gynecol 1990;76:58–60.

10. Corteville J E, Dicke J M, Crane J P. Fetal pyelectasis and Down syndrome: Is genetic amniocentesis warranted? Obstet Genecol 1992;79:770–2.

11. Benacerraf B R, Frigoletto F D. Soft tissue nuchal fold in the second-trimester fetus: Standards for normal measurements compared with those in Down syndrome. Am J Obstet Gynecol 1987; 157:1146–9.

12. Crane J P, Gray D L. Sonographically measured nuchal skinfold thickness as a screening tool for Down syndrome: Results of a prospective clinical trial. Obstet Gynecol 1991;77:533–6.

13. Scioscia A L, Pretorius D H, Budorick N E, Cahill T C, Axelrod FT, Leopold G R. Second trimester echogenic bowel and chromosomal abnormalities. Am J Obstet Gynecol 1992; 167:889–94.

14. Dicke J M, Crane J P. Sonographically defected hyperechoic fetal bowel: Significance and implications for pregnancy management. Obstet Gynecol 1992;80:778–82.

15. Benacerraf B R, Harlow B L, Frigoletto F D. Hypoplasia of the middle phalanx of the fifth digit. J Ultrasound Med 1990;9:389–94.

16. Nadel A S, Bromley B, Frigoletto F D, Benacerraf B R. Can the presumed risk of autosomal trisomy be decreased in fetuses of older women following a normal sonogram? J Ultrasound Med 1995;14:297–302.

17. Vintzileos A M, Egan J F X. Adjusting the risk for trisomy 21 on the basis of second trimester ultrasonography. Am J Obstet Gynecol 1995;172:83744.

18. Kramer M S. Clinical epidemiology and biostatistics. New York: Springer-Verlag, 1988:20119.

19. Peipert J F and Sweeney P J. Diagnostic testing in Obstetrics and Gynecology: A clinician's guide. Obstet Gynecol 1993;82:619–23.

20. Haddow J E, Palomaki G E, Knight G J, Cunningham G C, Lustig L S, Boyd P A. Reducing the need for amniocentesis in women 35 years of age or older with serum markers for screening. N Eng J Med 1994;330: 114–8.

The invention being thus described, it will be obvious that the same may be varied in many ways. Such variations are not to be regarded as a departure from the spirit and scope of the invention and all such modifications are intended to be included within the scope of the following claims.

We claim:

1. A method for the prenatal detection of trisomy 21 in the second trimester by fetal long bone biometry which comprises the steps of:
   (a) measuring ultrasonically the biparietal diameter and the length of the femur, humerus, tibia, and fibula bones in fetuses of a patient population in the second trimester;
   (b) performing amniocentesis on the patient population in step (a) to determine which fetuses are normal and which fetuses have trisomy 21;
   (c) from the normal fetuses, deriving equations describing the predicted lengths of the femur, humerus, tibia, and fibula based on the biparietal diameter measurements;
   (d) calculating a ratio of observed lengths to predicted lengths of the femur, humerus, tibia, and fibula for all fetuses;
   (e) comparing the ratios calculated in step (d) for normal fetuses against the ratios calculated for fetuses having trisomy 21 and determining a threshold, as a percentile of these ratios, for abnormally short bone lengths in the fetuses having trisomy 21; and
   (f) employing the threshold determined in step (e) to detect prenatally trisomy 21 by fetal long bone biometry.

2. The method according to claim 1, wherein step (c) is performed with a computer software program.

3. The method according to claim 1, wherein steps (d) is performed with a computer software program.

4. The method according to claim 1, wherein steps (e) is performed with a computer software program.

5. A method for the prenatal detection of trisomy 21 in the second trimester by adjusting the risk of trisomy 21 based on fetal long bone biometry which comprises the steps of:
   (a) measuring ultrasonically the biparietal diameter and the length of the femur, humerus, tibia, and fibula bones in fetuses of a patient population in the second trimester;
   (b) performing amniocentesis on the patient population in step (a) to determine which fetuses are normal and which fetuses have trisomy 21;
   (c) from the normal fetuses, deriving equations describing the predicted lengths of the femur, humerus, tibia, and fibula based on the biparietal diameter measurements;
   (d) calculating a ratio of observed lengths to predicted lengths of the femur, humerus, tibia, and fibula for all fetuses;
   (e) comparing the ratios calculated in step (d) for normal fetuses against the ratios calculated for fetuses having trisomy 21 and determining a threshold, as a percentile of these ratios, for abnormally short bone lengths in the fetuses having trisomy 21;
   (f) employing the threshold determined in step (e) to determine sensitivity and specificity in detecting prenatally trisomy 21 by fetal long bone biometry; and
   (g) employing the sensitivity and specificity determined in step (f) to adjust the risk of trisomy 21.

6. The method according to claim 2, wherein step (c) is performed with a computer software program.

7. The method according to claim 2, wherein steps (d) is performed with a computer software program.

8. The method according to claim 2, wherein steps (e) is performed with a computer software program.

9. The method according to claim 2, wherein steps (f) is performed with a computer software program.

* * * * *